United States Patent
Liu et al.

(10) Patent No.: US 10,578,572 B2
(45) Date of Patent: Mar. 3, 2020

(54) CMOS INTEGRATED MICROHEATER FOR A GAS SENSOR DEVICE

(71) Applicant: INVENSENSE, INC., San Jose, CA (US)

(72) Inventors: Fang Liu, San Jose, CA (US); Jim Salvia, Redwood City, CA (US); Zhineng Zhu, Fremont, CA (US); Michael Perrott, Nashua, NH (US)

(73) Assignee: INVENSENSE, INC., San Jose, CA (US)

( * ) Notice: Subject to any disclaimer, the term of this patent is extended or adjusted under 35 U.S.C. 154(b) by 0 days.

(21) Appl. No.: 15/000,729

(22) Filed: Jan. 19, 2016

(65) Prior Publication Data

US 2017/0205368 A1    Jul. 20, 2017

(51) Int. Cl.
| | |
|---|---|
| G01N 27/04 | (2006.01) |
| G01N 27/14 | (2006.01) |
| H01L 23/34 | (2006.01) |
| G01N 27/12 | (2006.01) |

(52) U.S. Cl.
CPC ............ *G01N 27/14* (2013.01); *G01N 27/046* (2013.01); *G01N 27/123* (2013.01); *G01N 27/128* (2013.01); *H01L 23/345* (2013.01)

(58) Field of Classification Search
CPC .................................................... G01N 27/046
USPC ........................................................ 257/467
See application file for complete search history.

(56) References Cited

U.S. PATENT DOCUMENTS

| | | | |
|---|---|---|---|
| 4,229,415 A | 10/1980 | Bryson | |
| 5,409,839 A | 4/1995 | Balestrieri et al. | |
| 5,724,256 A | 3/1998 | Lee et al. | |
| 5,776,425 A | 7/1998 | Wu et al. | |
| 6,111,280 A | 8/2000 | Gardner et al. | |
| 6,161,421 A | 12/2000 | Fang et al. | |
| 6,259,350 B1* | 7/2001 | Mueller-Fiedler | .... C04B 41/009 338/25 |
| 6,282,458 B1 | 8/2001 | Murayama et al. | |
| 6,347,414 B2 | 2/2002 | Contadini et al. | |
| 6,553,777 B2 | 4/2003 | Dillenback | |
| 6,628,204 B1 | 9/2003 | Ito | |

(Continued)

FOREIGN PATENT DOCUMENTS

| | | |
|---|---|---|
| CN | 104316566 A | 1/2015 |
| EP | 2762864 A1 | 8/2014 |
| GB | 2464016 A | 4/2010 |

OTHER PUBLICATIONS

Frey, et al., "A Digital CMOS Architecture for a Micro-Hotplate Array," IEEE Journal of Solid-State Circuits, vol. 42, No. 2, Feb. 2007, 10 pages.

(Continued)

*Primary Examiner* — Hsin Yi Hsieh
(74) *Attorney, Agent, or Firm* — Amin, Turocy & Watson, LLP

(57) ABSTRACT

A gas sensor device with temperature uniformity is presented herein. In an implementation, a device includes a complementary metal-oxide semiconductor (CMOS) substrate layer, a dielectric layer and a gas sensing layer. The dielectric layer is deposited on the CMOS substrate layer. Furthermore, the dielectric layer includes a temperature sensor and a heating element coupled to a heat transfer layer associated with a set of metal interconnections. The gas sensing layer is deposited on the dielectric layer.

20 Claims, 10 Drawing Sheets

(56) References Cited

U.S. PATENT DOCUMENTS

| | | | |
|---|---|---|---|
| 6,861,939 | B1 | 3/2005 | Bischof et al. |
| 7,610,118 | B2 | 10/2009 | Schramm et al. |
| 8,392,029 | B2 | 3/2013 | Nakamoto et al. |
| 9,352,065 | B2 | 5/2016 | Habbel |
| 9,377,786 | B2 | 6/2016 | Nakamoto et al. |
| 9,439,995 | B2 | 9/2016 | Conroy et al. |
| 9,691,214 | B2 | 6/2017 | Chan et al. |
| 9,827,343 | B2 | 11/2017 | Lima et al. |
| 9,860,690 | B2 | 1/2018 | Bak et al. |
| 2001/0029781 | A1* | 10/2001 | Tai ................ G01F 1/6845 73/204.26 |
| 2002/0119093 | A1 | 8/2002 | Murayama et al. |
| 2003/0039586 | A1 | 2/2003 | Toyoda et al. |
| 2005/0185392 | A1 | 8/2005 | Walter et al. |
| 2005/0199041 | A1 | 9/2005 | Weber et al. |
| 2006/0154401 | A1 | 7/2006 | Gardner et al. |
| 2006/0231882 | A1 | 10/2006 | Kim et al. |
| 2007/0258849 | A1 | 11/2007 | Kent |
| 2009/0126460 | A1* | 5/2009 | Gardner ............ G01N 33/0031 73/31.06 |
| 2010/0044453 | A1 | 2/2010 | Porchia et al. |
| 2011/0226864 | A1 | 9/2011 | Kim et al. |
| 2012/0046790 | A1 | 2/2012 | Anderson |
| 2012/0288987 | A1 | 11/2012 | Radu et al. |
| 2013/0075255 | A1 | 3/2013 | Moon et al. |
| 2014/0208828 | A1* | 7/2014 | Von Waldkirch .... G01N 27/123 73/25.05 |
| 2014/0208830 | A1* | 7/2014 | Buhler ............ H01L 21/28556 73/31.06 |
| 2015/0056426 | A1 | 2/2015 | Grouchko et al. |
| 2016/0038908 | A1 | 2/2016 | Cobianu et al. |
| 2016/0187279 | A1 | 6/2016 | Tayebi et al. |
| 2016/0187280 | A1 | 6/2016 | Potyralio et al. |
| 2016/0370263 | A1 | 12/2016 | Duesterhoft et al. |
| 2017/0067841 | A1 | 3/2017 | Liu et al. |
| 2017/0168000 | A1 | 6/2017 | Ichiki |
| 2018/0028985 | A1 | 2/2018 | Ansley et al. |

OTHER PUBLICATIONS

Partial International Search Report dated Oct. 25, 2016 for PCT Application Serial No. PCT/US2016/047359, 8 pages.

Simon, et al., "Micromachined Metal Oxide Gas Sensors: Opportunities to Improve Sensor Performance", Sensors and Actuators B: Chemical: International Journal Devoted to Research and Development of Physical and Chemical Transducers, Elsevier BV, NL, vol. B73, No. 1, Feb. 25, 2001 (Feb. 25, 2001), pp. 1-26, XP001120244.

Bhattacharyya, "Technological Journey Towards Reliable Microheater Development for MEMS Gas Sensors: A Review," IEEE Transactions on Device and Materials Reliability, vol. 14, No. 2, Jun. 2014, 11 pages.

Office Action for U.S. Appl. No. 14/849,551 dated May 30, 2017, 25 pages.

Office Action for U.S. Appl. No. 14/849,551 dated Jul. 27, 2017, 16 pages.

Wilson, et al., "Applications and Advances in Electronic-Nose Technologies," Sensors 9.7 (2009): pp. 5099-5148.

Nakaizumi, et al., "SpotScents: A Novel Method of Natural Scent Delivery Using Multiple Scent Projectors." Virtual Reality Conference, 2006. IEEE, 2006. 6 pages.

Nakamoto, et al., "Study of odor recorder for dynamical change of odor using QCM sensors and neural network," Sensors and Actuators B: Chemical 85.3 (2002): pp. 263-269.

Choi, et al, "The Wireless Electronic Noses and Mobile Devices Interoperation Based on Internet of Things Technology," Advanced Science and Technology Letters vol. 120 (GST 2015), pp. 149-152.

Office Action for U.S. Appl. No. 15/365,818 dated May 18, 2018, 40 pages.

Internation Search Report and Written Opinion dated Apr. 3, 2017 for International Application Serial No. PCT/US2017/1013885, 14 pages.

Afridi M et al: "Transient heating study of microhotplates by using a high-speed thermal imaging system", 18th Annual IEEE Semiconductor Thermal Measurement and Management Symposium. Semi-Therm. Proceedings 2002. San Jose, CA, Mar. 2002; [IEEE Semiconductor Thermal Measurement and Management Symposium. Semi-Therm], New York, NY IEEE, US, Mar. 12, 2002 (Mar. 12, 2002), pp. 92-98, XP032155652.

Ansys, "Thermal Solutions for 3-D IC, Packages and Systems", Jan. 1, 2013 (Jan. 1, 2013), XP055358498, Retrieved from the Internet: URL:http://resource.ansys.com/staticassets /ANSYS/staticassets/ resourcelibrary/techbrief/tb-thermal-solutions-for-3d-ic-pkg-and-sys. pdf [retrieved on Mar. 24, 2017] the whole document.

Office Action for U.S. Appl. No. 15/047,344 dated Jun. 5, 2018, 43 pages.

Office Action for U.S. Appl. No. 16/038,499 dated Oct. 1, 2018, 22 pages.

Office Action for U.S. Appl. No. 14/849,551 dated Jan. 18, 2018, 10 pages.

Final Office Action received for U.S. Appl. No. 15/047,344 dated Dec. 11, 2018, 27 pages.

Final Office Action received for U.S. Appl. No. 15/365,818 dated Dec. 13, 2018, 25 pages.

Final Office Action for U.S. Appl. No. 14/849,551 dated Feb. 14, 2019, 25 pages.

Final Office Action for U.S. Appl. No. 16/038,499 dated Feb. 27, 2019, 23 pages.

Non-Final Office Action for U.S. Appl. No. 16/038,499 dated Jun. 25, 2019, 15 pages.

Non-Final Office Action for U.S. Appl. No. 15/047,344 dated Jun. 27, 2019, 37 pages.

Final Office Action for U.S. Appl. No. 16/038,499 dated Nov. 20, 2019, 36 pages.

* cited by examiner

CMOS INTEGRATED MICROHEATER FOR A GAS SENSOR DEVICE

TECHNICAL FIELD

The subject disclosure relates generally to a gas sensor device.

BACKGROUND

Certain gas sensors rely on physical changes or chemical changes in a chemical sensing material while in the presence of a gas to determine concentration of the gas in a surrounding environment. Further, certain chemical sensing materials preferentially operate at a temperature above normal ambient or room temperatures. However, incorporating a conventional heater in a gas sensor device can cause damage to other integrated components of the gas sensor device, increase cost of the gas sensor device and/or increase power consumption of the gas sensor device.

SUMMARY

The following presents a simplified summary of the specification to provide a basic understanding of some aspects of the specification. This summary is not an extensive overview of the specification. It is intended to neither identify key or critical elements of the specification nor delineate any scope particular to any embodiments of the specification, or any scope of the claims. Its sole purpose is to present some concepts of the specification in a simplified form as a prelude to the more detailed description that is presented later.

In accordance with an implementation, a device includes a complementary metal-oxide semiconductor (CMOS) substrate layer, a dielectric layer and a gas sensing layer. The dielectric layer is deposited on the CMOS substrate layer. Furthermore, the dielectric layer includes a temperature sensor and a heating element coupled to a heat transfer layer associated with a set of metal interconnections. The gas sensing layer is deposited on the dielectric layer.

In accordance with another implementation, a device includes at least a dielectric layer and a gas sensing layer. The dielectric layer is deposited on a silicon substrate layer. Furthermore, the dielectric layer includes a temperature sensor and a heating element coupled to a heat transfer layer associated with a set of metal interconnections. The gas sensing layer is deposited on the dielectric layer, where the heating element provides heat to the gas sensing layer.

In accordance with yet another implementation, a device includes at least a dielectric layer and a gas sensing layer. The dielectric layer is deposited on a silicon substrate layer. Furthermore, the dielectric layer includes a temperature sensor and a heating element coupled to a heat transfer layer associated with a set of metal interconnections, where the temperature sensor is associated with a first resistance and the heating element is associated with a second resistance. The gas sensing layer is deposited on the dielectric layer.

These and other embodiments are described in more detail below.

BRIEF DESCRIPTION OF THE DRAWINGS

Various non-limiting embodiments are further described with reference to the accompanying drawings, in which.

DETAILED DESCRIPTION

Overview

Figure 1:
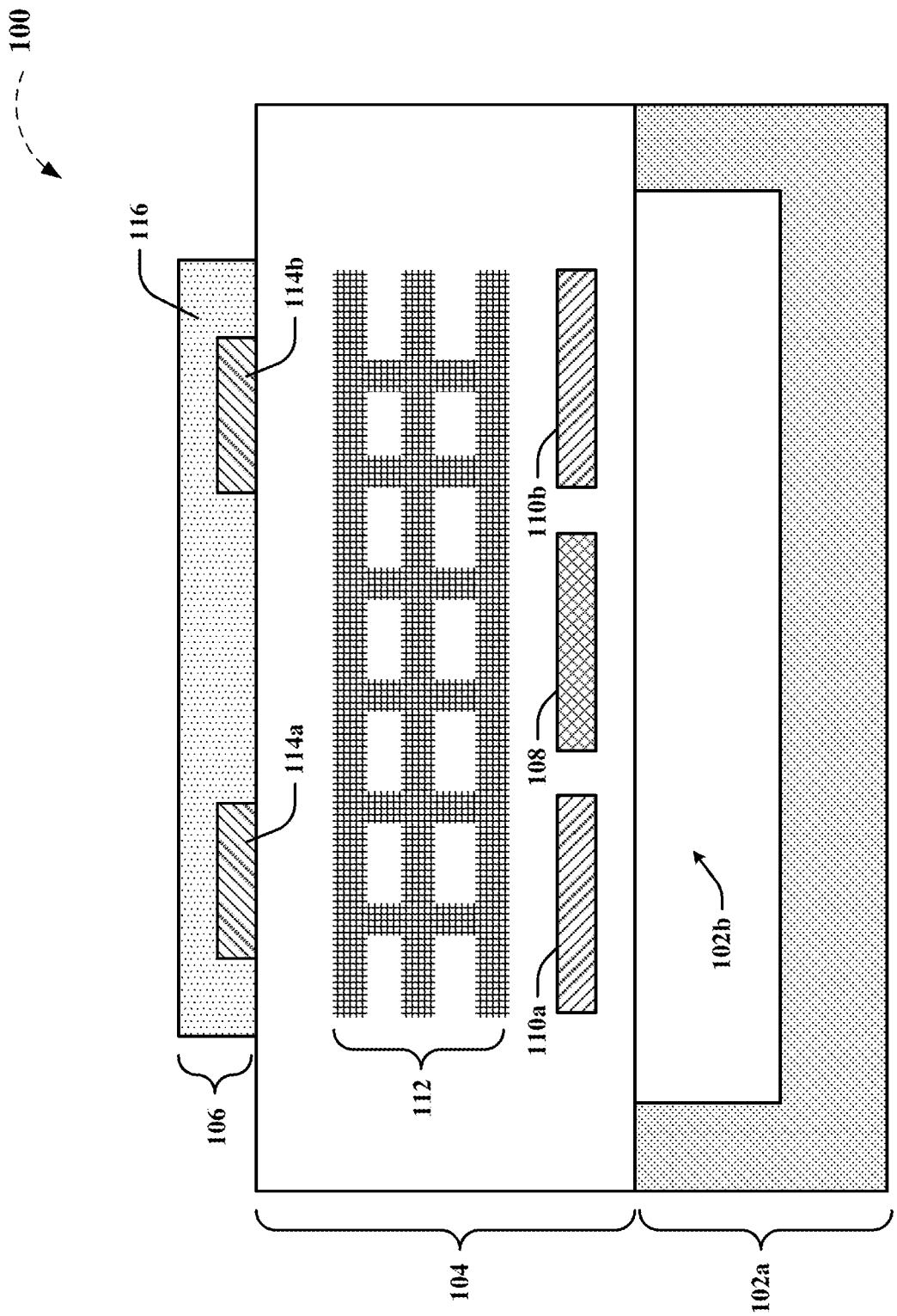
FIG. 1 depicts a cross-sectional view of a gas sensor device, in accordance with various aspects and implementations described herein.

While a brief overview is provided, certain aspects of the subject disclosure are described or depicted herein for the purposes of illustration and not limitation. Thus, variations of the disclosed embodiments as suggested by the disclosed apparatuses, systems, and methodologies are intended to be encompassed within the scope of the subject matter disclosed herein.

As described above, certain gas sensors rely on physical or chemical changes in a chemical sensing material while in the presence of a gas to determine concentration of the gas in a surrounding environment. Further, certain chemical sensing materials preferentially operate at a temperature above normal ambient or room temperatures. However, incorporating a conventional heater in a gas sensor device can cause damage to other integrated components of the gas sensor device, increase cost of the gas sensor device and/or increase power consumption of the gas sensor device.

To these and/or related ends, various aspects and embodiments of a complementary metal-oxide-semiconductor (CMOS) integrated microheater are described. The various embodiments of the systems, techniques, and methods of the subject disclosure are described in the context of a gas sensor device (e.g., a gas sensing device) configured for sensing a gas in a surrounding environment. In an embodiment, a gas sensor device comprises a microheater suspended in a CMOS portion (e.g., a CMOS dielectric layer) of the gas sensor device. The microheater can comprise poly-silicon (e.g., a poly-silicon metal gate) as a heating element and/or a temperature sensing element for gas sensing applications. In an aspect, the microheater can comprise a heater resistor (e.g., a heater resistor that comprises a released structure). The heater resistor can comprise a higher resistance at edges of the heater resistor that are coupled to a substrate (e.g., a CMOS substrate) of the gas sensor device. Other edges of the heater resistor can comprise a lower resistance. Additionally, the microheater can comprise a temperature sensor resistor. The temperature sensor resistor can comprise a higher resistance using lower doping or a non-silicidation method at a center of a heating area of the microheater to improve temperature sensing accuracy of the gas sensor device. Resistance design of the microheater (e.g. resistance design of a heater and a temperature sensor of the gas sensor device) can be varied based on geometry and/or a type of poly-silicon (e.g., selective salicides of gate poly-silicon resistor). Accordingly, in-plane temperature uniformity for the gas sensor can be realized. Moreover, by employing a heater and a temperature sensor in a CMOS portion (e.g., a CMOS layer) of the gas sensor device, the microheater can be easily integrated with a heater control circuit of the gas sensor device. Cost of the gas sensor device (e.g., size and/or cost of a die) can also be reduced and/or temperature feedback control of the gas sensor device can also be improved. Furthermore, risk of damage to other integrated components of the gas sensor device and/or power consumption of the gas sensor device can be reduced.

In an implementation, metal vias (e.g., aluminum vias, tungsten vias, other metal vias, etc.) can be formed in the CMOS portion (e.g., the CMOS dielectric layer) of the gas sensor device. The metal vias can provide improved temperature uniformity at both an in-plane direction and an out-of-plane direction of the mircoheater. The gas sensor device can comprise, for example, a gas sensing layer contact (e.g., a noble metal) that is electrically coupled to a gas sensing material of the gas sensor device (e.g., a gas sensing material deposited on a top layer of the gas sensor device). However, as further detailed below, various exemplary implementations can be applied to other areas of a gas sensor device, without departing from the subject matter described herein.

Exemplary Embodiments

Various aspects or features of the subject disclosure are described with reference to the drawings, wherein like reference numerals are used to refer to like elements throughout. In this specification, numerous specific details are set forth in order to provide a thorough understanding of the subject disclosure. It should be understood, however, that the certain aspects of disclosure may be practiced without these specific details, or with other methods, components, parameters, etc. In other instances, well-known structures and devices are shown in block diagram form to facilitate description and illustration of the various embodiments.

FIG. 1 depicts a cross-sectional view of a gas sensor device 100, according to various non-limiting aspects of the subject disclosure. The gas sensor device 100 can be gas sensor with a uniform temperature design (e.g., distribution of temperature in the gas sensor device 100 can be uniform). The gas sensor device 100 includes a CMOS substrate layer 102a, a dielectric layer 104 and a gas sensing layer 106. The dielectric layer 104 can be deposited or formed on the CMOS substrate layer 102a. For example, the dielectric layer 104 can be etched to the CMOS substrate layer 102a via wet etching or dry etching. Furthermore, the etching of the dielectric layer 104 to the CMOS substrate can be an isotropic etch or an anisotropic etch (e.g., a deep reactive ion etching, etc.). The CMOS substrate layer 102a can include a cavity 102b. The cavity 102b can thermally isolate the dielectric layer 104.

The dielectric layer 104 can provide mechanical support for temperature sensing elements and/or heating elements of the gas sensor device 100. The dielectric layer 104 can include a temperature sensor 108 and a heating element 110a-b. In one example, the heating element 110a-b can be implemented as a microheater. The temperature sensor 108 can be employed to sense temperature of the heating element 110a-b (e.g., the microheater). As such, the temperature sensor 108 and the heating element 110a-b can be implemented separate from the CMOS substrate layer 102a for improved thermal isolation (e.g., a micro-bridge structure associated with the heating element 110a-b can be outside of the CMOS substrate layer 102a for improved thermal isolation). In a non-limiting example, a thickness of the dielectric layer 104 can be approximately equal to 10 microns. However, it is to be appreciated that the dielectric layer 104 can comprise a different thickness.

The heating element 110a-b includes a first heating element 110a and a second heating element 110b. The temperature sensor 108 can be implemented between the first heating element 110a and the second heating element 110b in the same film deposition process. Film of the film deposition process can be, for example, polycrystalline silicon with different doping levels and/or metal silicide. Furthermore, the heating element 110a-b can be implemented as a micro-bridge structure. For example, the first heating element 110a can be configured as a first micro-bridge structure and the second heating element 110b can be configured as a second micro-bridge structure. The heating element 110a-b can also be electrically connected in a parallel resistor configuration. In one example, the first micro-bridge structure of the first heating element 110a can correspond to the second micro-bridge structure of the second heating element 110b. In another example, the first micro-bridge structure of the first heating element 110a can be different than the second micro-bridge structure of the second heating element 110b. In an aspect, the heating element 110a-b can be a resistive heating element. For example, the heating element 110a-b can be implemented as a resistive structure to generate an amount of heat (e.g., an amount of heat for the gas sensing layer 106). In one example, the first heating element 110a can be configured as a first resistive structure to generate a first amount of heat and the second heating element 110b can be configured as a second resistive structure to generate a second amount of heat. The first resistive structure of the first heating element 110a can correspond to the second resistive structure of the second heating element 110b. Alternatively, the first resistive structure of the first heating element 110a can be different than the second resistive structure of the second heating element 110b.

Resistance of the heating element 110a-b can be tuned based on a geometry of the heating element 110a-b (e.g., a geometry of poly-silicon of the heating element 110a-b). For example, resistance of the first heating element 110a can be tuned based on a geometry (e.g., a shape) of the first heating element 110a and resistance of the second heating element 110b can be tuned based on a geometry (e.g., a shape) of the second heating element 110a. Additionally or alternatively, resistance of the heating element 110a-b can be tuned based on doping level(s) of the heating element 110a-b. For example, resistance of the first heating element 110a can be tuned based on doping level(s) of the first heating element 110*a* and resistance of the second heating element 110*b* can be tuned based on doping level(s) of the second heating element 110*a*. In an aspect, a first portion of the heating element 110*a-b* (e.g., a portion of the heating element 110*a-b* that is associated with the temperature sensor 108) can comprise a different resistance than one or more other portions of the heating element 110*a-b* (e.g., a portion of the heating element 110*a-b* that is not associated with the temperature sensor 108).

The temperature sensor 108 can be configured to sense temperature associated with the gas sensing layer 106. For example, the temperature sensor 108 can be configured as a resistive structure to sense temperature associated with the gas sensing layer 106. Resistance of the temperature sensor 108 can be tuned based on doping level(s) of the temperature sensor 108. Additionally or alternatively, resistance of the temperature sensor 108 can be tuned based on a silicidation process associated with the temperature sensor 108. Furthermore, the temperature sensor 108 and the heating element 110*a-b* can both comprise poly-silicon. In an aspect, the temperature sensor 108 can be associated with a first resistance and the heating element 110*a-b* can be associated with a second resistance. In another aspect, the temperature sensor 108 can comprise a first type of poly-silicon and the heating element 110*a-b* can comprise a second type of poly-silicon. For example, the temperature sensor 108 can comprise poly-silicon associated with a first resistance and the heating element 110*a-b* can comprise poly-silicon associated with a second resistance that is lower than the first resistance. As such, improved in-plane temperature uniformity for the gas sensor device 100 can be achieved. In an aspect, a first portion of the temperature sensor 108 (e.g., a center portion of the temperature sensor 108) can comprise a different resistance than one or more other portions of the temperature sensor 108 (e.g., outer portions of the temperature sensor 108).

The temperature sensor 108 and the heating element 110*a-b* can be electrically and/or thermally coupled to a heat transfer layer 112. The heat transfer layer 112 can be associated with a set of metal interconnections (e.g., a set of metal vias). For example, the heat transfer layer 112 can comprise a set of metal interconnections that comprises aluminum, tungsten or another type of metal. Furthermore, the heat transfer layer 112 can include a plurality of metal layers that are electrically coupled via the set of metal interconnections. In an implementation, the temperature sensor 108, the heating element 110*a-b* and/or the heat transfer layer 112 can be suspended in the dielectric layer 104. For example, the temperature sensor 108, the heating element 110*a-b* and/or the heat transfer layer 112 can be surrounded by a dielectric material of the dielectric layer 104. As such, both in-plane temperature uniformity and out-of-plane temperature uniformity can be achieved for the gas sensor device 100. The heat transfer layer 112 can transfer heat from a bottom portion of the dielectric layer 104 (e.g., a bottom portion of the dielectric layer 104 that is associated with the CMOS substrate layer 102*a*) to a top portion of the dielectric layer 104 (e.g., a top portion of the dielectric layer 104 that is associated with the gas sensing layer 106).

The gas sensing layer 106 can be deposited or formed on the dielectric layer 104. The gas sensing layer 106 can include a set of gas-sensing contacts 114*a-b* and a gas-sensing material 116. The gas-sensing contacts 114*a-b* can be electrically coupled to the gas-sensing material 116. In an aspect, the gas-sensing contacts 114*a-b* and at least a portion of the gas-sensing material 116 can be deposited or formed on the dielectric layer 104. The gas-sensing contacts 114*a-b* can be contact electrodes. The gas-sensing contacts 114*a-b* can be employed to detect changes in the gas-sensing material 116. For example, the gas-sensing contacts 114*a-b* can be employed to detect changes in the gas-sensing material 116 as a concentration of a target gas changes. The gas-sensing contacts 114*a-b* can be made of a conductive material, such as a noble metal. For example, the gas-sensing contacts 114*a-b* can comprise titanium nitride, poly-silicon, tungsten, another metal, etc. In one example, the gas-sensing contacts 114*a-b* can be electrically coupled to another component (e.g., an application-specific integrated circuit (ASIC)) of the gas sensor device 100.

The gas-sensing material 116 can be thermally coupled to the heating element 110*a-b* (e.g., the heating element 110*a-b* can provide heat to the gas-sensing material 116 of the gas sensing layer 106). For example, the dielectric layer 104 can provide thermal coupling between the heating element 110*a-b* and the gas-sensing material 116 so that the heat provided by the heating element 110*a-b* is conducted to the gas-sensing material 116. Accordingly, dielectric material of the dielectric layer 104 is preferably a low k dielectric material (e.g., a low k dielectric material relative to the CMOS substrate layer 102*a* and/or the gas sensing layer 106) with certain thermal conductivity. Furthermore, the gas-sensing material 116 can be exposed to an environment surrounding the gas sensor device 100. For illustration, the gas sensor device 100 can be associated with a sensor pixel (e.g., a single sensor pixel). For example, the gas-sensing material 116 can be configured sense a type and/or a concentration of a certain gas. However, it is to be appreciated that the gas sensor device 100 can be configured with more than one sensor pixel that comprises one or more types of sensor pixels. Therefore, the gas sensor device 100 can be configured to detect numerous different gases at various concentrations.

Furthermore, the gas-sensing material 116 can comprise a metal oxide having an electrical resistance based on a concentration of a gas in an environment surrounding the gas sensor device 100 and/or an operating temperature of the gas-sensing material 116. The gas-sensing material 116 can comprise an operating temperature greater than room temperature and determined by an amount of heat generated by the heating element 110*a-b*. In one example, the gas-sensing material 116 can be a chemical sensing material. The gas-sensing material 116 can comprise a metal oxide, such as but not limited to, an oxide of chromium, manganese, nickel, copper, tin, indium, tungsten, titanium, vanadium, iron, germanium, niobium, molybdenum, tantalum, lanthanum, cerium or neodymium. Alternatively, the gas-sensing material 116 can be composite oxides including binary, ternary, quaternary and complex metal oxides. The gas-sensing material 116 can be employed to detect chemical changes (e.g., chemical changes in response to a gas). For example, a conductivity change associated with the gas-sensing material 116 can be employed to detect a gas. In another example, a change of electrical resistance of the gas-sensing material 116 can be employed to detect a gas. In yet another example, a change of capacitance associated with the gas-sensing material 116 can be employed to detect a gas. However, it is to be appreciated that other changes associated with the gas-sensing material 116 (e.g., a change in work function, a change in mass, a change in optical characteristics, a change in reaction energy, etc.) can be additionally or alternatively employed to detect a gas. The gas-sensing material 116 can be formed through techniques such as printing, sputter deposition, chemical vapor deposition, epitaxial growth and/or another technique.

In an aspect, the gas sensor device 100 can employ the heating element 110a-b since the gas-sensing material 116 may only be sufficiently sensitive at a high temperature. For example, the operating temperature of some gas-sensing material is ideally above 100 degrees Celsius to achieve sensitivity sufficient for robust measurement. Moreover, different gas-sensing materials may have different activation temperatures, and the heating element 110a-b can be employed to optimize conditions for a given gas. In one example, the gas-sensing material 116 can comprise an operating temperature or an activation temperature at which, or above which, sensitivity of the gas-sensing material 116 reaches a desired threshold. In another aspect, the temperature sensor 108 can be configured to measure temperature of the gas-sensing material 116. The temperature sensor 108 can also provide feedback for temperature control. For example, the temperature sensor 108 can supply an electrical signal in response to an operating temperature of the gas-sensing material 116. In an implementation, a portion of the CMOS substrate layer 102a can be etched or otherwise removed to create the cavity 102b. The cavity 102b can be a thermal isolation cavity that thermally isolates the dielectric layer 104 and/or the gas sensing layer 106 from a bulk of the CMOS substrate layer 102a. The cavity 102b of the CMOS substrate layer 102a can allow integration of the dielectric layer 104 and/or the gas sensing layer 106 with other devices (e.g., an ASIC) and/or protects other devices from heat produced by the heating element 110a-b.

Figure 2:
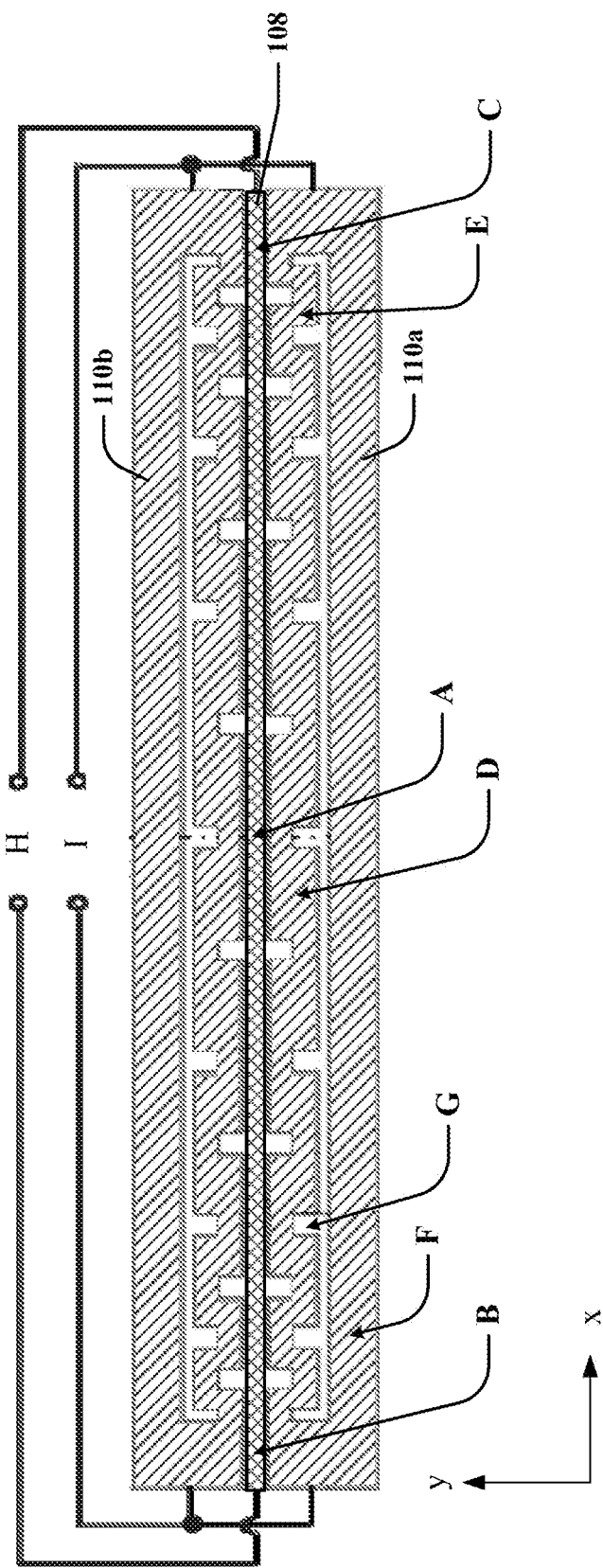
FIG. 2 depicts a cross-sectional view of a heating element and a temperature sensor, in accordance with various aspects and implementations described herein.

FIG. 2 depicts the temperature sensor 108 and the heating element 110a-b, according to various non-limiting aspects of the subject disclosure. The temperature sensor 108 and the heating element 110a-b of FIG. 2 can be suspended in the dielectric layer 104. The temperature sensor 108 can be configured as a temperature sensor resistor comprising poly-silicon (e.g., gate poly-silicon). Furthermore, the heating element 110a-b can be configured as a heater resistor comprising poly-silicon (e.g., gate poly-silicon).

The temperature sensor 108 can comprise a higher resistance at a center portion A of the temperature sensor 108, as compared to a portion B and a portion C of the temperature sensor 108. For example, the center portion A of the temperature sensor 108 can comprise a different doping level than the portion B and the portion C of the temperature sensor 108. In another example, resistance of the center portion A, the portion B and the portion C of the temperature sensor 108 can be configured based on a silicidation process associated with the temperature sensor 108. Accordingly, at the center portion A, temperature can be uniform to improve linearity and/or accuracy of temperature monitoring by the temperature sensor 108.

Different locations of the heating element 110a-b can also comprise different resistances. For example, a portion D of the first heating element 110a can comprise a different resistance than a portion E of the first heating element 110a. For example, the portion D of the first heating element 110a can comprise a different geometry (e.g., a different shape) than the portion E of the first heating element 110a, resulting in different resistances for the portion D and the portion E of the first heating element 110a. In another example, the portion D of the first heating element 110a can comprise a different doping level than the portion E of the first heating element 110a, resulting in different resistances for the portion D and the portion E of the first heating element 110a. Furthermore, a portion F of the first heating element 110a can comprise a different resistance than the portion D and the portion E of the first heating element 110a. For example, the portion F of the first heating element 110a can comprise a different geometry (e.g., a different shape) than the portion D and the portion E of the first heating element 110a. In another example, the portion F of the first heating element 110a can comprise a different doping level than the portion D and the portion E of the first heating element 110a. In addition, feedback control of temperature of the heating element 110a-b can be realized by circular design of the heating element 110a and the heating element 110b. For example, a poly-silicon portion of the first heating element 110a (e.g., a poly-silicon portion of the first heating element 110a that includes the portion D, the portion E, the portion F, etc.) can comprise a void portion G at a center (e.g., in the middle) of the poly-silicon portion of the first heating element 110a.

As such, the temperature sensor 108 and the heating element 110a-b shown in FIG. 2 can provide a uniform temperature design for the gas sensor device 100. For example, a higher power input to compensate for thermal loss can occur at edges of the temperature sensor 108 and/or heating element 110a-b. Along an x direction shown in FIG. 2, voltage is constant. Furthermore, resistance can be higher at edges of the temperature sensor 108 and the heating element 110a-b along the x direction shown in FIG. 2. Along a y direction shown in FIG. 2, current is constant. Furthermore, resistance can be lower at edges of the temperature sensor 108 and the heating element 110a-b along the y direction shown in FIG. 2. In an aspect, the temperature sensor 108 and/or the heating element 110a-b (e.g., edges of the heating element 110a-b) can be coupled to the CMOS substrate layer 102a and/or another component of the gas sensor device 100. For example, the temperature sensor 108 can be coupled to the CMOS substrate layer 102a and/or another component of the gas sensor device 100 (e.g., an ASIC) via terminal point H. Furthermore, the first heating element 110a and the second heating element 110b can be coupled to the CMOS substrate layer 102a and/or another component of the gas sensor device 100 (e.g., an ASIC) via terminal point I.

Figure 3:
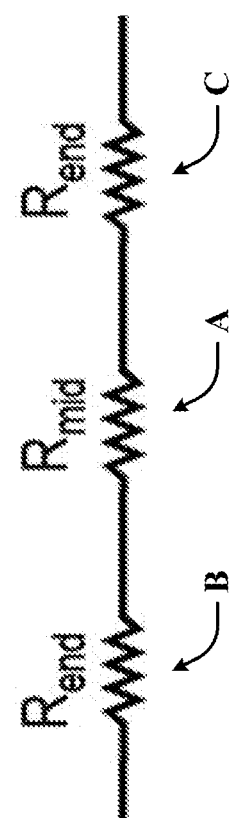
FIG. 3 depicts a schematic diagram representing resistances associated with a temperature sensor, in accordance with various aspects and implementations described herein.

FIG. 3 depicts a schematic diagram 300 representing resistances associated with the temperature sensor 108. For example, the schematic diagram 300 can correspond to a resistive micro-bridge structure for the temperature sensor 108. The schematic diagram 300 includes resistors $R_{end}$ and a resistor $R_{mid}$. The resistors $R_{end}$ and the resistor $R_{mid}$ can correspond to different locations of the temperature sensor 108. For example, the resistors $R_{end}$ can correspond to end portions of the temperature sensor 108 and the resistor $R_{mid}$ can correspond to a center portion of the temperature sensor 108. In a non-limiting example, resistor $R_{mid}$ can correspond to the center portion A of the temperature sensor 108 shown in FIG. 2, and the resistors $R_{end}$ can correspond to the portion B and the portion C of the temperature sensor 108 shown in FIG. 2. The resistors $R_{end}$ can comprise a different resistance than the resistor $R_{mid}$. As such, different locations of the temperature sensor 108 can correspond to different resistances.

In one example, the resistors $R_{end}$ can comprise a lower resistance than the resistor $R_{mid}$. To achieve the lower resistance, the resistors $R_{end}$ can comprise a different doping level than the resistor $R_{mid}$. Alternatively, the resistors $R_{end}$ can comprise a different resistance than the resistor $R_{mid}$ via a silicidation process associated with the temperature sensor 108. In one example, resistance difference between the resistors $R_{end}$ and the resistor $R_{mid}$ can be achieved by using silicide/poly for the resistors $R_{end}$ and non-silicide/poly for the resistor $R_{mid}$. Therefore, overall resistance of the temperature sensor 108 can be equal to $(2 \cdot R_{end} + R_{mid})$, where resistance of the temperature sensor 108 is more greatly influenced by $R_{mid}$. For example, changes in $R_{mid}$ can have a greater impact on overall resistance of the temperature sensor 108 than similar changes in $R_{end}$. This can be beneficial for increasing measurement sensitivity in a region of gas sensor material (e.g., the gas-sensing material 116) relative to region outside of a gas sensor material.

Figure 4:
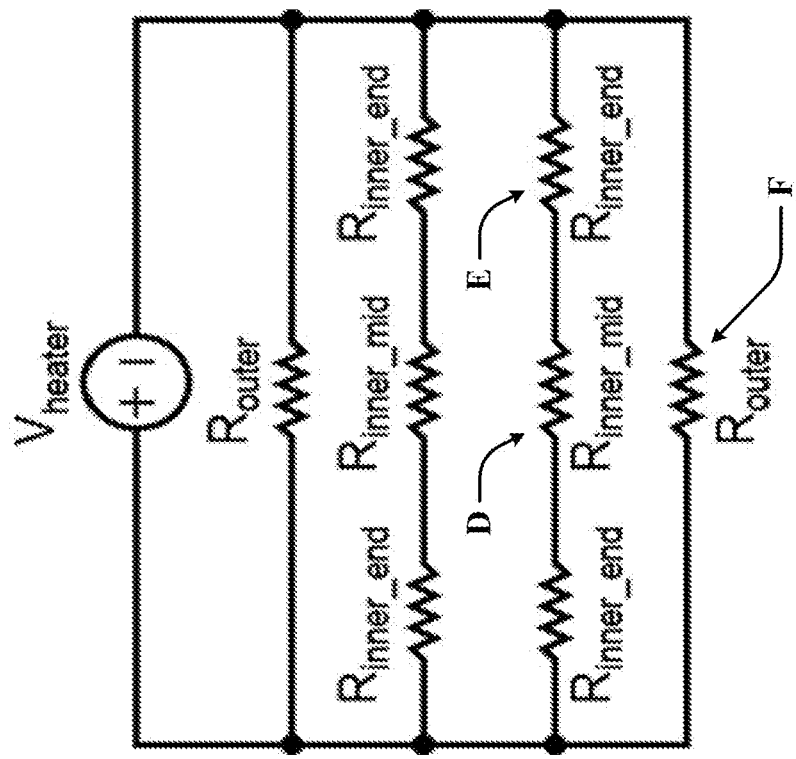
FIG. 4 depicts a schematic diagram representing resistances associated with a heating element, in accordance with various aspects and implementations described herein.

FIG. 4 depicts a schematic diagram 400 representing resistances associated with the heating element 110a-b. For example, the schematic diagram 400 can correspond to a resistive micro-bridge structure for the heating element 110a and the heating element 110b. The schematic diagram 400 includes a voltage source $V_{heater}$, resistors $R_{outer}$, resistors $R_{inner\_end}$, and resistors $R_{inner\_mid}$. The voltage source $V_{heater}$ can provide electrical energy to the heating element 110a-b. The heating element 110a-b can convert the electrical energy provided by the voltage source $V_{heater}$ into heat (e.g., thermal energy). The resistors $R_{outer}$, the resistors $R_{inner\_end}$, and the resistors $R_{inner\_mid}$ can correspond to different locations of the heating element 110a and the heating element 110b. For example, the resistors $R_{outer}$ can correspond to portions of the heating element 110a-b that are not associated with the temperature sensor 108. Furthermore, the resistors $R_{inner\_end}$ and the resistors $R_{inner\_mid}$ can correspond to portions of the heating element 110a-b that are associated with the temperature sensor 108. In a non-limiting example, resistor $R_{inner\_mid}$ can correspond to the portion D of the first heating element 110a shown in FIG. 2, resistor $R_{inner\_end}$ can correspond to the portion E of the first heating element 110a shown in FIG. 2, and resistor $R_{outer}$ can correspond to the portion F of the first heating element 110a shown in FIG. 2. The resistors $R_{outer}$, the resistors $R_{inner\_end}$, and the resistors $R_{inner\_mid}$ can each comprise different resistances. As such, different locations of the heating element 110a-b can correspond to different resistances.

In one example, the resistors $R_{inner\_mid}$ can comprise a lower resistance than the resistors $R_{inner\_mid}$. Therefore, more power can be allocated to a left edge and a right edge of the schematic diagram 400 (e.g., a left edge and a right edge of the heating element 110a and the heating element 110b). To achieve the lower resistance, the resistors $R_{inner\_mid}$ can comprise a different geometry (e.g., a different shape) than the resistors $R_{inner\_end}$. Alternatively, the resistors $R_{inner\_mid}$ can comprise a different doping level than the resistors $R_{inner\_mid}$. Furthermore, the resistors $R_{outer}$ can comprise a lower resistance than a resistance equal to $(2 \cdot R_{inner\_end} + R_{inner\_mid})$. To achieve the lower resistance, the resistors $R_{outer}$ can comprise a different geometry (e.g., a different shape) than the resistors $R_{inner\_end}$ and the resistors $R_{inner\_mid}$. Alternatively, the resistors $R_{outer}$ can comprise a different doping level than the resistors $R_{inner\_end}$ and the resistors $R_{inner\_mid}$. Accordingly, more power can be allocated to an upper edge and a lower edge of the schematic diagram 400 (e.g., an upper edge and a lower edge of the heating element 110a and the heating element 110b).

Figure 5:
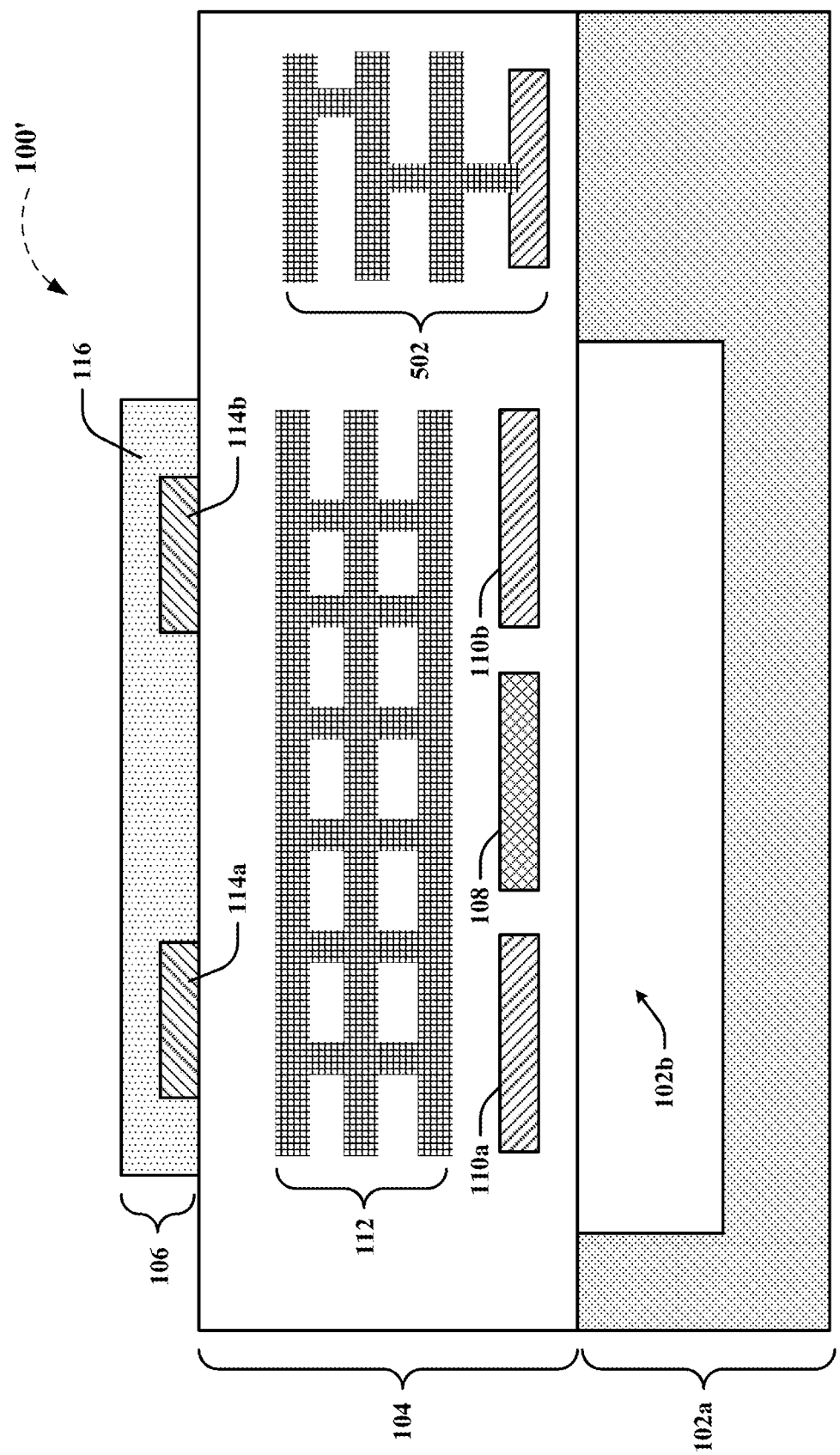
FIG. 5 depicts another cross-sectional view of a gas sensor device, in accordance with various aspects and implementations described herein.

FIG. 5 depicts a cross-sectional view of a gas sensor device 100', according to various non-limiting aspects of the subject disclosure. The gas sensor device 100' includes the CMOS substrate layer 102a, the dielectric layer 104 and the gas sensing layer 106. In an implementation, the CMOS substrate layer 102a can include the cavity 102b. The dielectric layer 104 can include the temperature sensor 108, the heating element 110a-b and the heat transfer layer 112. The gas sensing layer 106 can include the set of gas-sensing contacts 114a-b and the gas-sensing material 116. The gas sensor device 100' can also include ASIC 502. The ASIC 502 can be fabricated in the dielectric layer 104 (e.g., with the temperature sensor 108, the heating element 110a-b and the heat transfer layer 112). Both the dielectric layer 104 and the ASIC 502 can be deposited or formed on the CMOS substrate layer 102a. The ASIC 502 can be mechanically coupled to the CMOS substrate layer 102a. It is to be appreciated that the ASIC 502 can comprise one or more ASIC devices.

The ASIC 502 can be configured for controlling heating of the heating element 110a-b, evaluating temperature associated with the gas-sensing material 116, determining concentrations of chemicals associated with the gas-sensing material 116, etc. In an implementation, the ASIC 502 can include integrated circuitry configured to supply an electrical current to the heating element 110a-b (e.g., so that heating element 110a-b can generate an amount of heat based on the electrical current supplied by the ASIC 502). For example, the ASIC 502 can be a heater control circuit. In one example, the voltage source $V_{heater}$ shown in FIG. 4 can be associated with the ASIC 502. In another implementation, the ASIC 502 can include integrated circuitry configured to control an operational temperature of the heating element 110a-b. In yet another implementation, the ASIC 502 can include integrated circuitry configured to measure changes associated with the gas-sensing material 116 (e.g., measure electrical resistance of the gas-sensing material 116, etc). For example, the ASIC 502 can be electrically coupled to the gas-sensing contacts 114a-b.

Figure 6:
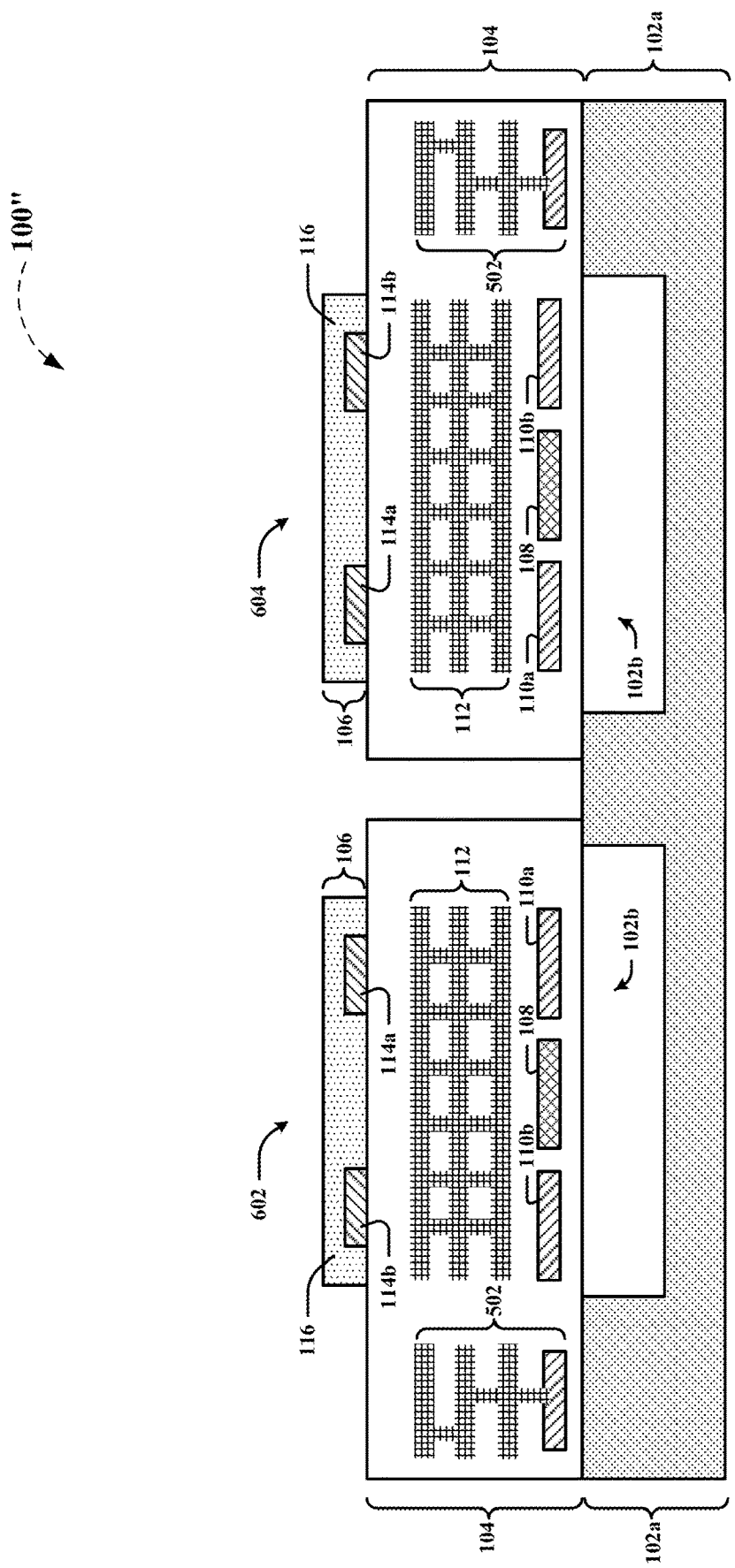
FIG. 6 depicts yet another cross-sectional view of a gas sensor device, in accordance with various aspects and implementations described herein.

FIG. 6 depicts a cross-sectional view of a gas sensor device 100", according to various non-limiting aspects of the subject disclosure. The gas sensor device 100" includes the CMOS substrate layer 102a, the ASIC(s) 502, a first sensor pixel 602 and a second sensor pixel 604. In an implementation, the CMOS substrate layer 102a can include more than one cavity 102b (e.g., two cavities 102b). The first sensor pixel 602 includes the dielectric layer 104 and the gas sensing layer 106. The dielectric layer 104 of the first sensor pixel 602 can include the temperature sensor 108, the heating element 110a-b and the heat transfer layer 112. Furthermore, the gas sensing layer 106 of the first sensor pixel 602 can include the set of gas-sensing contacts 114a-b and the gas-sensing material 116. Similarly, the second sensor pixel 604 includes the dielectric layer 104 and the gas sensing layer 106. The dielectric layer 104 of the second sensor pixel 604 can include the temperature sensor 108, the heating element 110a-b and the heat transfer layer 112. Furthermore, the gas sensing layer 106 of the second sensor pixel 604 can include the set of gas-sensing contacts 114a-b and the gas-sensing material 116. In an implementation, the gas sensing layer 106 of the first sensor pixel 602 can be configured to sense a first type of gas and the gas sensing layer 106 of the second sensor pixel 604 can be configured to sense a second type of gas. In another implementation, the gas sensing layer 106 of the first sensor pixel 602 and the gas sensing layer 106 of the second sensor pixel 604 can be configured to sense a corresponding type of gas. In one example, the first sensor pixel 602 and the second sensor pixel 604 can each be associated with an ASIC 502. Alternatively, the first sensor pixel 602 and the second sensor pixel 604 can be associated with a corresponding ASIC 502.

While various embodiments for a gas sensor device according to aspects of the subject disclosure have been described herein for purposes of illustration, and not limitation, it can be appreciated that the subject disclosure is not so limited. Various implementations can be applied to other devices and/or other gas sensing applications, without departing from the subject matter described herein. Furthermore, various exemplary implementations of systems as described herein can additionally, or alternatively, include other features, functionalities and/or components and so on.

In view of the subject matter described supra, methods that can be implemented in accordance with the subject disclosure will be better appreciated with reference to the flowcharts of FIGS. 7-10. While for purposes of simplicity of explanation, the methods are shown and described as a series of blocks, it is to be understood and appreciated that such illustrations or corresponding descriptions are not limited by the order of the blocks, as some blocks may occur in different orders and/or concurrently with other blocks from what is depicted and described herein. Any non-sequential, or branched, flow illustrated via a flowchart should be understood to indicate that various other branches, flow paths, and orders of the blocks, can be implemented which achieve the same or a similar result. Moreover, not all illustrated blocks may be required to implement the methods described hereinafter.

Exemplary Methods

Figure 7:
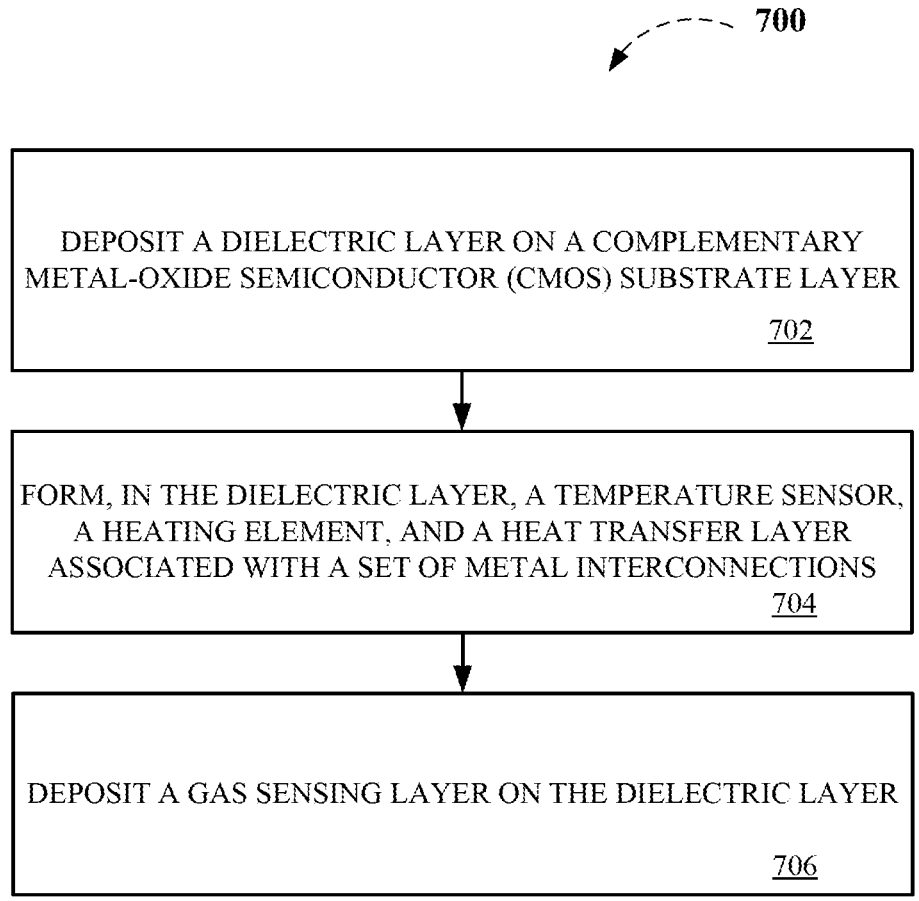
FIG. 7 is a flowchart of an example methodology for providing uniform temperature in a gas sensor, in accordance with various aspects and implementations described herein.

FIG. 7 depicts an exemplary flowchart of a non-limiting method 700 for providing uniform temperature in a gas sensor, according to various non-limiting aspects of the subject disclosure. In an aspect, the method 700 can be associated with the gas sensor device 100, the gas sensor device 100' and/or the gas sensor device 100". Initially, at 702, a dielectric layer is deposited on a complementary metal-oxide semiconductor (CMOS) substrate layer. Dielectric material of the dielectric layer can comprise a low k dielectric value with respect to the CMOS substrate layer and/or a silicon material (e.g., silicon dioxide). In one example, the dielectric layer can be etched to the CMOS substrate layer via wet etching. In another example, the dielectric layer can be etched to the CMOS substrate layer via dry etching.

At 704, a temperature sensor, a heating element, and a heat transfer layer associated with a set of metal interconnections are formed in the dielectric layer. For example, the temperature sensor, the heating element, and the heat transfer layer can be suspended and/or embedded in the dielectric layer. The temperature sensor and the heating element can both comprise poly-silicon. For example, the temperature sensor can comprise first poly-silicon with a resistance that is higher than a resistance of second poly-silicon of the heating element. Resistance of the temperature sensor can be tuned based on doping level and/or a silicidation process associated with the temperature sensor. Resistance of the heating element can be tuned based on doping level and/or a geometry (e.g., a shape) associated with the heating element. In an implementation, the temperature sensor can be implemented between a first heating element portion of the heating element and a second heating element portion of the heating element.

At 706, a gas sensing layer is deposited on the dielectric layer. For example, a set of gas-sensing contacts and gas-sensing material can be deposited on the dielectric layer. The gas-sensing material can be thermally coupled to the heating element included in the dielectric layer. The gas-sensing contacts can be contact electrodes. The gas-sensing contacts can be made of a conductive material, such as a noble metal (e.g., titanium nitride, poly-silicon, tungsten, another metal, etc.). Furthermore, the gas-sensing contacts can be employed to detect changes in the gas-sensing material in response to exposure to a particular gas in an environment. The gas-sensing material can be a chemical sensing material. The gas-sensing material can comprise a metal oxide, such as but not limited to, an oxide of chromium, manganese, nickel, copper, tin, indium, tungsten, titanium, vanadium, iron, germanium, niobium, molybdenum, tantalum, lanthanum, cerium or neodymium. Alternatively, the gas-sensing material can be composite oxides including binary, ternary, quaternary and complex metal oxides. The gas-sensing material can be formed via a printing technique, a sputter deposition technique, a chemical vapor deposition technique, an epitaxial growth technique and/or another technique.

Figure 8:
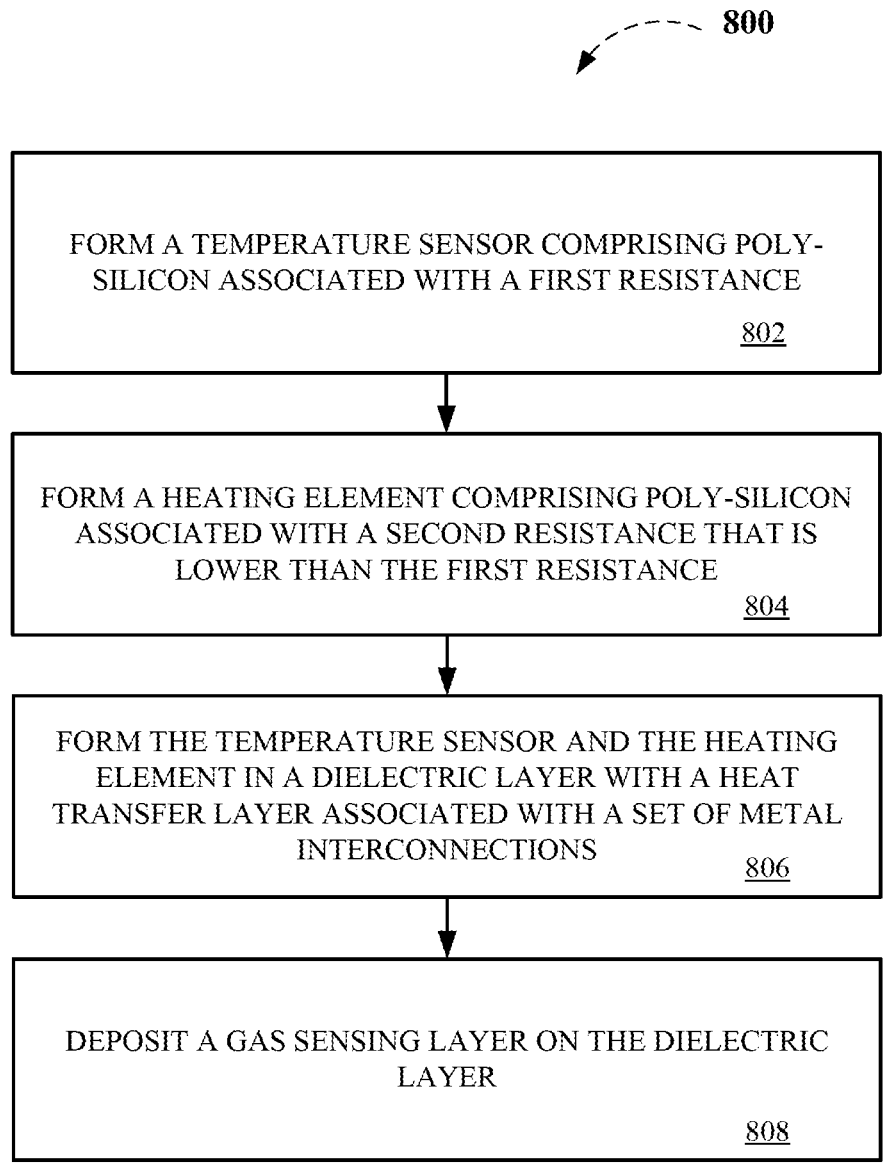
FIG. 8 is a flowchart of an example methodology for providing a microheater of a gas sensor with uniform temperature, in accordance with various aspects and implementations described herein.

FIG. 8 depicts an exemplary flowchart of a non-limiting method 800 for providing a microheater of a gas sensor with uniform temperature, according to various non-limiting aspects of the subject disclosure. In an aspect, the method 800 can be associated with the gas sensor device 100, the gas sensor device 100' and/or the gas sensor device 100". Initially, at 802, a temperature sensor comprising poly-silicon associated with a first resistance is formed. The first resistance of the temperature sensor can be tuned based on a doping level the poly-silicon associated with the temperature sensor. Additionally or alternatively, the first resistance of the temperature sensor can be tuned based on a silicidation process associated with the temperature sensor. In an aspect, a first portion of the temperature sensor (e.g., a center portion of the temperature sensor) can comprise a different resistance than one or more other portions of the temperature sensor (e.g., outer portions of the temperature sensor).

At 804, a heating element comprising poly-silicon associated with a second resistance that is lower than the first resistance is formed. The second resistance of the heating element can be tuned based on a geometry associated with the heating element (e.g., a shape of the poly-silicon associated with the heating element). Additionally or alternatively, the second resistance of the heating element can be tuned based on a doping level the poly-silicon associated with the heating element. In an aspect, a first portion of the heating element (e.g., a portion of the heating element that is associated with the temperature sensor) can comprise a different resistance than one or more other portions of the heating element (e.g., a portion of the heating element that is not associated with the temperature sensor).

At 806, the temperature sensor and the heating element are formed in a dielectric layer with a heat transfer layer associated with a set of metal interconnections. For example, the temperature sensor, the heating element and the heat transfer layer can be suspended in the dielectric layer (e.g., the temperature sensor, the heating element and the heat transfer layer can be surrounded by dielectric material of the dielectric layer). The dielectric layer can be formed or deposited on a CMOS substrate layer. Dielectric material of the dielectric layer can comprise a low k dielectric value with respect to the CMOS substrate layer and/or a silicon material (e.g., silicon dioxide). The temperature sensor and the heating element can be electrically and/or thermally coupled to a heat transfer layer.

At 808, a gas sensing layer is deposited on the dielectric layer. For example, a set of gas-sensing contacts and gas-sensing material can be deposited on the dielectric layer. The gas-sensing material can be thermally coupled to the heating element included in the dielectric layer. The gas-sensing contacts can be contact electrodes. The gas-sensing contacts can be made of a conductive material, such as a noble metal (e.g., titanium nitride, poly-silicon, tungsten, another metal, etc.). Furthermore, the gas-sensing contacts can be employed to detect changes in the gas-sensing material in response to exposure to a particular gas in an environment. The gas-sensing material can be a chemical sensing material. The gas-sensing material can comprise a metal oxide, such as but not limited to, an oxide of chromium, manganese, nickel, copper, tin, indium, tungsten, titanium, vanadium, iron, germanium, niobium, molybdenum, tantalum, lanthanum, cerium or neodymium. Alternatively, the gas-sensing material can be composite oxides including binary, ternary, quaternary and complex metal oxides.

Figure 9:
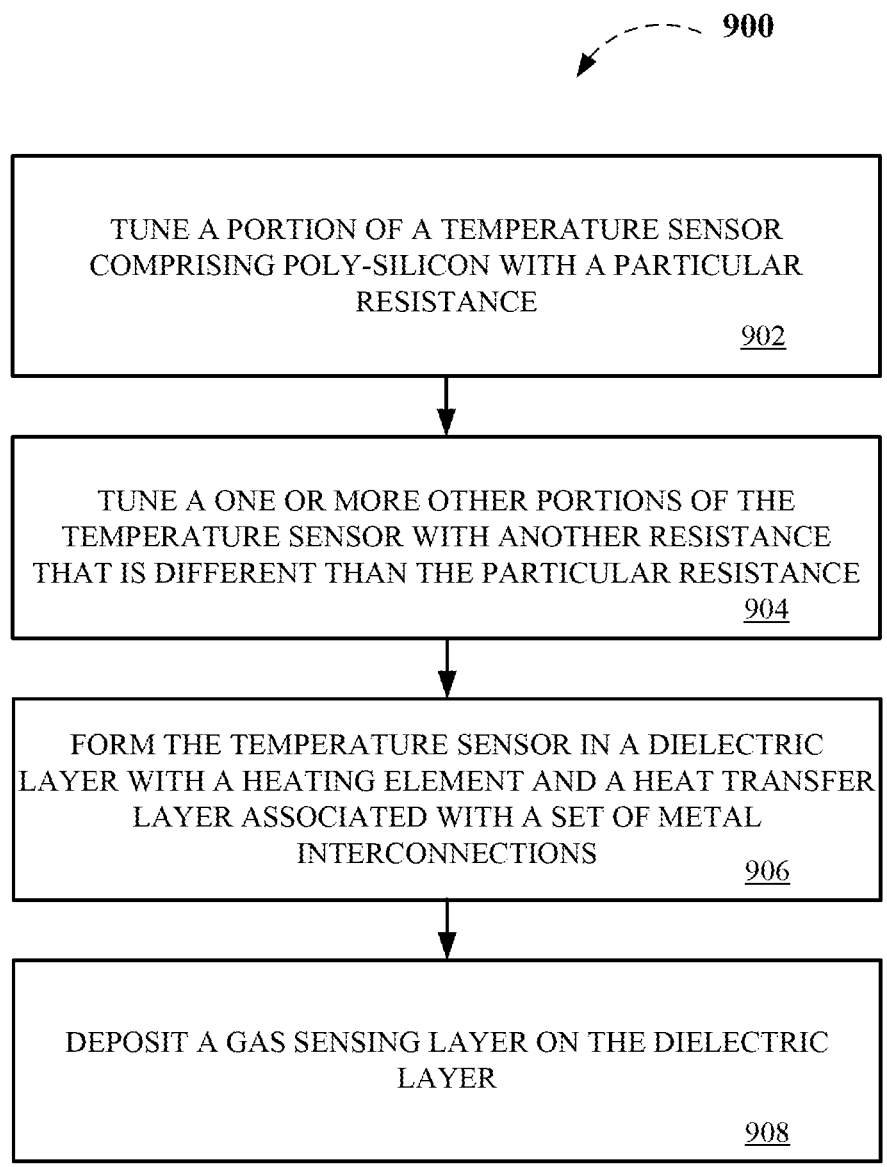
FIG. 9 is a flowchart of an example methodology for tuning a resistance of a temperature sensor, in accordance with various aspects and implementations described herein.

FIG. 9 depicts an exemplary flowchart of a non-limiting method 900 for tuning a resistance of a temperature sensor, according to various non-limiting aspects of the subject disclosure. In an aspect, the method 900 can be associated with the gas sensor device 100, the gas sensor device 100' and/or the gas sensor device 100''. Initially, at 902, a portion of a temperature sensor comprising poly-silicon is tuned with a particular resistance. For example, the poly-silicon of the portion of the temperature sensor can be tuned with a particular doping level. Alternatively, poly-silicon of the portion of the temperature sensor can be tuned to the particular resistance based on a silicidation process.

At 904, one or more other portions of the temperature sensor are tuned with another resistance that is different than the particular resistance. For example, poly-silicon of the one or more other portions of the temperature sensor can be tuned with one or more other doping levels. Alternatively, poly-silicon of the one or more other portions of the temperature sensor can be tuned to other resistances based on a silicidation process.

At 906, the temperature sensor is formed in a dielectric layer with a heating element and a heat transfer layer associated with a set of metal interconnections. For example, the temperature sensor, the heating element and the heat transfer layer can be suspended in the dielectric layer (e.g., the temperature sensor, the heating element and the heat transfer layer can be surrounded by dielectric material of the dielectric layer). The dielectric layer can be formed or deposited on a CMOS substrate layer. Dielectric material of the dielectric layer can comprise a low k dielectric value with respect to the CMOS substrate layer and/or a silicon material (e.g., silicon dioxide). The temperature sensor and the heating element can be electrically and/or thermally coupled to a heat transfer layer.

At 908, a gas sensing layer is deposited on the dielectric layer. The gas-sensing material can be thermally coupled to the heating element included in the dielectric layer. The gas-sensing contacts can be contact electrodes. The gas-sensing contacts can be made of a conductive material, such as a noble metal (e.g., titanium nitride, poly-silicon, tungsten, another metal, etc.). Furthermore, the gas-sensing contacts can be employed to detect changes in the gas-sensing material in response to exposure to a particular gas in an environment. The gas-sensing material can be a chemical sensing material. The gas-sensing material can comprise a metal oxide, such as but not limited to, an oxide of chromium, manganese, nickel, copper, tin, indium, tungsten, titanium, vanadium, iron, germanium, niobium, molybdenum, tantalum, lanthanum, cerium or neodymium. Alternatively, the gas-sensing material can be composite oxides including binary, ternary, quaternary and complex metal oxides.

Figure 10:
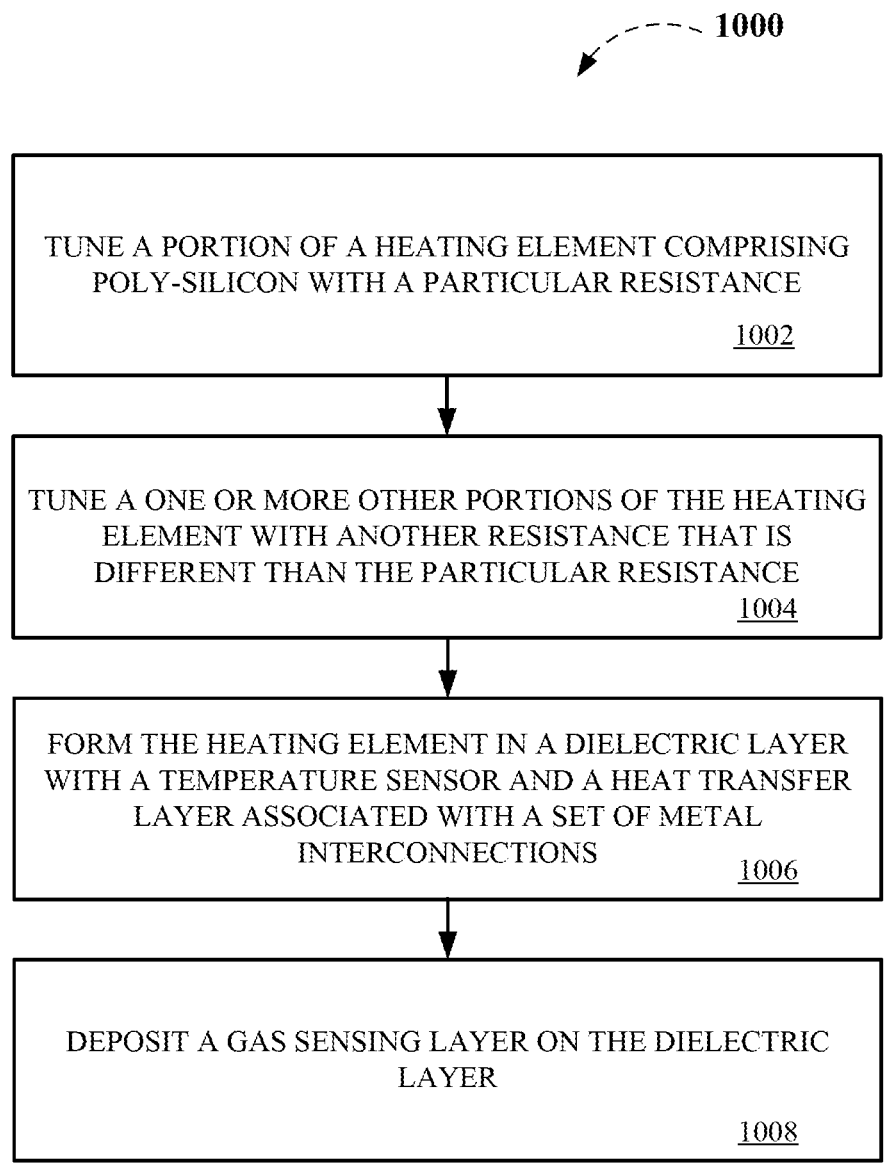
FIG. 10 is a flowchart of an example methodology for tuning a resistance of a heating element, in accordance with various aspects and implementations described herein.

FIG. 10 depicts an exemplary flowchart of a non-limiting method 1000 for tuning a resistance of a heating element, according to various non-limiting aspects of the subject disclosure. In an aspect, the method 1000 can be associated with the gas sensor device 100, the gas sensor device 100' and/or the gas sensor device 100''. Initially, at 1002, a portion of a heating element comprising poly-silicon is tuned with a particular resistance. For example, the poly-silicon of the portion of the heating element can formed with a particular shape (e.g., a particular geometry). Alternatively, the poly-silicon of the portion of the heating element can be tuned with a particular doping level.

At 1004, one or more other portions of the heating element are tuned with another resistance that is different than the particular resistance. For example, poly-silicon of the one or more other portions of the heating element can be tuned with one or more other formed with a shapes (e.g., other geometries). Alternatively, poly-silicon of the one or more other portions of the heating element can be tuned with one or more other doping levels.

At 1006, the heating element is formed in a dielectric layer with a temperature sensor and a heat transfer layer associated with a set of metal interconnections. For example, the heating element, the temperature sensor and the heat transfer layer can be suspended in the dielectric layer (e.g., the heating element, the temperature sensor and the heat transfer layer can be surrounded by dielectric material of the dielectric layer). The dielectric layer can be formed or deposited on a CMOS substrate layer. Dielectric material of the dielectric layer can comprise a low k dielectric value with respect to the CMOS substrate layer and/or a silicon material (e.g., silicon dioxide). The heating element and the temperature sensor can be electrically and/or thermally coupled to a heat transfer layer.

At 1008, a gas sensing layer is deposited on the dielectric layer. The gas-sensing material can be thermally coupled to the heating element included in the dielectric layer. The gas-sensing contacts can be contact electrodes. The gas-sensing contacts can be made of a conductive material, such as a noble metal (e.g., titanium nitride, poly-silicon, tungsten, another metal, etc.). Furthermore, the gas-sensing contacts can be employed to detect changes in the gas-sensing material in response to exposure to a particular gas in an environment. The gas-sensing material can be a chemical sensing material. The gas-sensing material can comprise a metal oxide, such as but not limited to, an oxide of chromium, manganese, nickel, copper, tin, indium, tungsten, titanium, vanadium, iron, germanium, niobium, molybdenum, tantalum, lanthanum, cerium or neodymium. Alternatively, the gas-sensing material can be composite oxides including binary, ternary, quaternary and complex metal oxides.

It is to be appreciated that various exemplary implementations of exemplary methods 700, 800, 900 and 1000 as described can additionally, or alternatively, include other process steps for providing uniform temperature in a gas sensor, as further detailed herein, for example, regarding FIGS. 1-6.

What has been described above includes examples of the embodiments of the subject disclosure. It is, of course, not possible to describe every conceivable combination of configurations, components, and/or methods for purposes of describing the claimed subject matter, but it is to be appreciated that many further combinations and permutations of the various embodiments are possible. Accordingly, the claimed subject matter is intended to embrace all such alterations, modifications, and variations that fall within the spirit and scope of the appended claims. While specific embodiments and examples are described in subject disclosure for illustrative purposes, various modifications are possible that are considered within the scope of such embodiments and examples, as those skilled in the relevant art can recognize.

In addition, the words "example" or "exemplary" is used herein to mean serving as an example, instance, or illustration. Any aspect or design described herein as "exemplary" is not necessarily to be construed as preferred or advantageous over other aspects or designs. Rather, use of the word, "exemplary," is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

In addition, while an aspect may have been disclosed with respect to only one of several embodiments, such feature may be combined with one or more other features of the other embodiments as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

What is claimed is:

1. A device, comprising:
   a complementary metal-oxide semiconductor (CMOS) substrate layer;
   a dielectric layer deposited on the CMOS substrate layer, wherein the dielectric layer comprises a temperature sensor, wherein the dielectric layer comprises a first heating element and a second heating element coupled to a heat transfer layer associated with a set of metal interconnections, and wherein the temperature sensor is located between the first heating element and the second heating element in the dielectric layer; and
   a gas sensing layer deposited on the dielectric layer, wherein the first heating element comprises a first geometry of poly-silicon, wherein the second heating element comprises a second geometry of the poly-silicon that is different than the first geometry, and wherein a first resistance and a first shape for the first geometry associated with the first heating element is different than a second resistance and a second shape for the second geometry associated with the second heating element.

2. The device of claim 1, wherein the temperature sensor comprises a first type of poly-silicon and the heating element comprises a second type of poly-silicon.

3. The device of claim 1, wherein the dielectric layer separates the temperature sensor, the first heating element, and the second heating element from the CMOS substrate layer.

4. The device of claim 1, wherein the first heating element and the second heating element are configured as micro-bridge structures.

5. The device of claim 1, wherein the first heating element and the second heating element are configured as resistive structures to generate an amount of heat.

6. The device of claim 1, wherein the first heating element is further tuned based on a doping level of the first heating element.

7. The device of claim 1, wherein the temperature sensor is configured as a resistive structure to sense temperature associated with the gas sensing layer.

8. The device of claim 1, wherein a resistance of the temperature sensor is tuned based on a doping level of the temperature sensor.

9. The device of claim 1, wherein a resistance of the temperature sensor is tuned based on a silicidation process associated with the temperature sensor.

10. The device of claim 1, wherein the heat transfer layer comprises a plurality of metal layers that are electrically coupled via the set of metal interconnections.

11. The device of claim 1, wherein the gas sensing layer comprises a set of gas-sensing contacts electrically coupled to a gas-sensing material.

12. The device of claim 1, wherein the temperature sensor, the first heating element, the second heating element and the heat transfer layer are surrounded by a dielectric material of the dielectric layer.

13. A device, comprising:
    a dielectric layer deposited on a silicon substrate layer, the dielectric layer comprising a temperature sensor, a first heating element and a second heating element, wherein the first heating element and the second heating element are coupled to a heat transfer layer associated with a set of metal interconnections, and wherein the temperature sensor is arranged between the first heating element and the second heating element in the dielectric layer; and
    a gas sensing layer deposited on the dielectric layer, wherein the first heating element and the second heating element provide heat to the gas sensing layer, wherein the first heating element comprises a first geometry of poly-silicon, wherein the second heating element comprises a second geometry of the poly-silicon that is different than the first geometry, and wherein a first resistance and a first shape for the first geometry associated with the first heating element is different than a second resistance and a second shape for the second geometry associated with the second heating element.

14. The device of claim 13, wherein the first heating element and the second heating element provide heat to a gas-sensing material of the gas sensing layer.

15. The device of claim 13, wherein a first location of the temperature sensor is associated with a third resistance and a second location of the temperature sensor is associated with a fourth resistance.

16. The device of claim 15, wherein the third resistance is determined based on a first doping level and the fourth resistance is determined based on a second doping level.

17. The device of claim 13, wherein a first location of the first heating element is associated with the first resistance and a second location of the second heating element is associated with the second resistance.

18. A device, comprising:
    a dielectric layer deposited on a silicon substrate layer, the dielectric layer comprising a temperature sensor, a first heating element and a second heating element, wherein the first heating element and the second heating element are coupled to a heat transfer layer associated with a set of metal interconnections, wherein the temperature sensor is located between the first heating element and the second heating element in the dielectric layer, wherein the temperature sensor is associated with a first resistance, wherein the first heating element comprises a first geometry of poly-silicon, wherein the second heating element comprises a second geometry of the poly-silicon that is different than the first geometry, and wherein a second resistance for the first geometry associated with the first heating element is different than a third resistance for the second geometry associated with the second heating element; and a gas sensing layer deposited on the dielectric layer.

19. The device of claim 1, wherein the heat transfer layer is suspended in the dielectric layer and is located between the temperature sensor and the gas sensing layer.

20. The device of claim 13, wherein the heat transfer layer is surrounded by a dielectric material of the dielectric layer and is located between the temperature sensor and the gas sensing layer.

* * * * *